US012679791B2

(12) United States Patent
Suzuki

(10) Patent No.: US 12,679,791 B2
(45) **Date of Patent: \*Jul. 14, 2026**

---

(54) METHOD FOR STORING FLUORO-2-BUTENE

(71) Applicant: Resonac Corporation, Tokyo (JP)

(72) Inventor: Atsushi Suzuki, Tokyo (JP)

(73) Assignee: Resonac Corporation, Tokyo (JP)

( * ) Notice: Subject to any disclaimer, the term of this patent is extended or adjusted under 35 U.S.C. 154(b) by 561 days.

This patent is subject to a terminal disclaimer.

(21) Appl. No.: 18/031,542

(22) PCT Filed: Oct. 8, 2021

(86) PCT No.: PCT/JP2021/037429
§ 371 (c)(1),
(2) Date: Apr. 12, 2023

(87) PCT Pub. No.: WO2022/080275
PCT Pub. Date: Apr. 21, 2022

(65) Prior Publication Data
US 2023/0373889 A1 Nov. 23, 2023

(30) Foreign Application Priority Data
Oct. 15, 2020 (JP) ................................. 2020-173922

(51) Int. Cl.
*C07C 17/42* (2006.01)
(52) U.S. Cl.
CPC .................................... *C07C 17/42* (2013.01)
(58) Field of Classification Search
CPC .......... C07C 17/42; C07C 17/38; C07C 22/18
See application file for complete search history.

(56) References Cited

U.S. PATENT DOCUMENTS

| | | | |
|---|---|---|---|
| 5,929,293 | A | 7/1999 | Krespan et al. |
| 10,077,330 | B2 | 9/2018 | Van Der Puy et al. |
| 10,941,237 | B2 | 3/2021 | Van Der Puy et al. |
| 2010/0264116 | A1 | 10/2010 | Suzuki et al. |
| 2011/0237844 | A1 | 9/2011 | Tung et al. |

| | | | |
|---|---|---|---|
| 2012/0004475 | A1 | 1/2012 | Miller et al. |
| 2012/0323054 | A1 | 12/2012 | Knapp |
| 2015/0051426 | A1 | 2/2015 | Fukushima et al. |
| 2015/0294880 | A1 | 10/2015 | Anderson et al. |
| 2016/0009847 | A1 | 1/2016 | Van Der Puy et al. |
| 2016/0023034 | A1* | 1/2016 | Elsheikh .................. C09K 3/00 516/8 |
| 2017/0015607 | A1 | 1/2017 | Baldychev et al. |
| 2017/0103901 | A1 | 4/2017 | Shen et al. |
| 2018/0215690 | A1 | 8/2018 | Nappa et al. |
| 2019/0085115 | A1 | 3/2019 | Van Der Puy et al. |

FOREIGN PATENT DOCUMENTS

| | | |
|---|---|---|
| CN | 105008442 A | 10/2015 |
| CN | 108911947 A | 11/2018 |
| EP | 3 238 820 A1 | 11/2017 |
| JP | 2002-47218 A | 2/2002 |
| JP | 2008-81477 A | 4/2008 |
| JP | 2010-1244 A | 1/2010 |
| JP | 2011-136955 A | 7/2011 |
| JP | 2012-131731 A | 7/2012 |
| JP | 2017-125023 A | 7/2017 |
| JP | 2018-522908 A | 8/2018 |
| JP | 6451810 B2 | 1/2019 |
| JP | 2019-34972 A | 3/2019 |
| JP | 2020-132585 A | 8/2020 |
| WO | 97/02226 A1 | 1/1997 |

OTHER PUBLICATIONS

Rong Guobin, "Fundamentals of University Organic Chemistry", East China University of Science and Technology Press, 2006, second edition, pp. 105 (5 pages total).
Chen Fei, "China Fire-Fighting Manual", Shanghai Scientific & Technical Publishers, 2006, first edition, pp. 55 (5 pages total).

\* cited by examiner

*Primary Examiner* — Jafar F Parsa
(74) *Attorney, Agent, or Firm* — Sughrue Mion, PLLC

(57) ABSTRACT

Provided is a method for storing a fluoro-2-butene by which isomerization reaction is unlikely to proceed during storage. A fluoro-2-butene represented by general formula $C_4H_xF_y$, where x is 0 or more and 7 or less, y is 1 or more and 8 or less, and x+y is 8 contains or does not contain hydrogen fluoride as an impurity. The fluoro-2-butene is stored in a container in which the concentration of hydrogen fluoride is 100 ppm by volume or less in a gas phase portion when the fluoro-2-butene contains hydrogen fluoride.

5 Claims, No Drawings

METHOD FOR STORING FLUORO-2-BUTENE

This Application is a National Stage of International Application No. PCT/JP2021/037429 filed Oct. 8, 2021, claiming priority based on Japanese Patent
Application No. 2020-173922 filed Oct. 15, 2020.

TECHNICAL FIELD

The present invention relates to a method for storing a fluoro-2-butene.

BACKGROUND ART

Unsaturated fluorocarbons disclosed, for example, in PTLs 1 and 2 may be used as an etching gas for dry etching. Of the unsaturated fluorocarbons, a fluoro-2-butene has attracted attention as an etching gas usable in state-of-the-art dry etching processes.

CITATION LIST

Patent Literature

PTL 1: JP 6451810 B
PTL 2: JP 2019-034972 A

SUMMARY OF INVENTION

Technical Problem

Fluoro-2-butenes, however, have Z- and E-geometric isomers, and isomerization reaction may proceed during storage for a long time.

The present invention is intended to provide a method for storing a fluoro-2-butene by which isomerization reaction is unlikely to proceed during storage.

Solution to Problem

To solve the problems, aspects of the present invention are the following [1] to [3].

[1] A method for storing a fluoro-2-butene represented by general formula $C_4H_xF_y$ where x is 0 or more and 7 or less, y is 1 or more and 8 or less, and x+y is 8, in which the fluoro-2-butene contains or does not contain hydrogen fluoride as an impurity, and the fluoro-2-butene is stored in a container in which the concentration of hydrogen fluoride is 100 ppm by volume or less in a gas phase portion when the fluoro-2-butene contains hydrogen fluoride.

[2] The method for storing a fluoro-2-butene according to the aspect [1], in which the fluoro-2-butene is at least one selected from (Z)-1,1,1,4,4,4-hexafluoro-2-butene, (E)-1,1, 1,4,4,4-hexafluoro-2-butene, (Z)-1,1,1,2,4,4,4-heptafluoro-2-butene, (E)-1,1,1,2,4,4,4-heptafluoro-2-butene, (Z)-1,1,1, 2,3,4,4,4-octafluoro-2-butene, and (E)-1,1,1,2,3,4,4,4-octafluoro-2-butene.

[3] The method for storing a fluoro-2-butene according to the aspect [1] or [2], in which the fluoro-2-butene is stored at a temperature of −20° C. or more and 50° C. or less.

Advantageous Effects of Invention

According to the present invention, isomerization reaction of a fluoro-2-butene is unlikely to proceed during storage.

DESCRIPTION OF EMBODIMENTS

Embodiments of the present invention will now be described. The embodiments are merely examples of the present invention, and the present invention is not limited to the embodiments. Various modifications or improvements can be made in the embodiments, and such modifications and improvements can be encompassed by the present invention.

The method for storing a fluoro-2-butene pertaining to the present embodiment is a method for storing a fluoro-2-butene represented by general formula $C_4H_xF_y$ where x is 0 or more and 7 or less, y is 1 or more and 8 or less, and x+y is 8. In the method, the fluoro-2-butene contains or does not contain hydrogen fluoride (HF) as an impurity, and the fluoro-2-butene is stored in a container in which the concentration of hydrogen fluoride is 100 ppm by volume or less in a gas phase portion when the fluoro-2-butene contains hydrogen fluoride.

When a fluoro-2-butene contains hydrogen fluoride as an impurity, the catalytic action of hydrogen fluoride accelerates isomerization reaction of the fluoro-2-butene. Hence, a fluoro-2-butene containing hydrogen fluoride may be isomerized during storage, and the purity may decrease.

A fluoro-2-butene stored by the method for storing a fluoro-2-butene pertaining to the present embodiment contains no hydrogen fluoride or contains hydrogen fluoride at a small content and thus is unlikely to be isomerized even when stored for a long time, and the purity is unlikely to decrease. Accordingly, the fluoro-2-butene can be stably stored over a long time.

The technology disclosed in PTLs 1 and 2 does not consider the concentration of hydrogen fluoride in an unsaturated fluorocarbon. Hence, when a fluoro-2-butene is stored by the technology disclosed in PTLs 1 and 2, hydrogen fluoride may accelerate isomerization reaction of the fluoro-2-butene. As a result, the fluoro-2-butene may be isomerized during storage, and the purity may decrease.

Hereinafter, the method for storing a fluoro-2-butene pertaining to the present embodiment will be described in further detail.

Fluoro-2-Butene

The fluoro-2-butene pertaining to the present embodiment is represented by general formula $C_4H_xF_y$, and satisfies three requirements in the general formula: x is 0 or more and 7 or less; y is 1 or more and 8 or less; and x+y is 8. The fluoro-2-butene may be any type that satisfies the above requirements.

Specific examples of the fluoro-2-butene include (Z)-$CHF_2$—CF=CF—$CF_3$, (E)-$CHF_2$—CF=CF—$CF_3$, (Z)-$CF_3$—CH=CF—$CF_3$, (E)-$CF_3$—CH=CF—$CF_3$, (Z)-$CH_2F$—CF=CF—$CF_3$, (E)-$CH_2F$—CF=CF—$CF_3$, (Z)-$CHF_2$—CH=CF—$CF_3$, (E)-$CHF_2$—CH=CF—$CF_3$, (Z)-$CHF_2$—CF=CF—$CHF_2$, (E)-$CHF_2$—CF=CF—$CHF_2$, (Z)-$CF_3$—CH=CH—$CF_3$, (E)-$CF_3$—CH=CH—$CF_3$, (Z)-$CH_3$—CF=CF—$CF_3$, (E)-$CH_3$—CF=CF—$CF_3$, (Z)-$CH_2F$—CH=CF—$CF_3$, (E)-$CH_2F$—CH=CF—$CF_3$, (Z)-$CH_2F$—CF=CH—$CF_3$, (E)-$CH_2F$—CF=CH—$CF_3$, (Z)-$CH_2F$—CF=CF—$CHF_2$, (E)-$CH_2F$—CF=CF—$CHF_2$, (Z)-$CHF_2$—CH=CH—$CF_3$, (E)-$CHF_2$—CH=CH—$CF_3$, (Z)-$CHF_2$—CF=CH—$CHF_2$, (E)-$CHF_2$—CF=CH—$CHF_2$, (Z)-$CH_3$—CH=CF—$CF_3$, (E)-$CH_3$—CH=CF—$CF_3$, (Z)-$CH_3$—CF=CH—$CF_3$, (E)-$CH_3$—CF=CH—$CF_3$, (Z)-$CH_3$—CF=CF—$CHF_2$, (E)-$CH_3$—CF=CF—$CHF_2$, (Z)-$CH_2F$—CH=CH—$CF_3$, (E)-$CH_2F$—CH=CH—$CF_3$, (Z)-CH$_2$F—CH=CF—CHF$_2$, (E)-CH$_2$F—CH=CF—CHF$_2$, (Z)-CH$_2$F—CF=CH—CHF$_2$, (E)-CH$_2$F—CF=CH—CHF$_2$, (Z)-CH$_2$F—CF=CF—CH$_2$F, (E)-CH$_2$F—CF=CF—CH$_2$F, (Z)-CHF$_2$—CH=CH—CHF$_2$, (E)-CHF$_2$—CH=CH—CHF$_2$, (Z)-CH$_3$—CH=CH—CF$_3$, (E)-CH$_3$—CH=CH—CF$_3$, (Z)-CH$_3$—CH=CF—CHF$_2$, (E)-CH$_3$—CH=CF—CHF$_2$, (Z)-CH$_3$—CF=CH—CHF$_2$, (E)-CH$_3$—CF=CH—CHF$_2$, (Z)-CH$_3$—CF=CF—CH$_2$F, (E)-CH$_3$—CF=CF—CH$_2$F, (Z)-CH$_2$F—CF=CH—CH$_2$F, (E)-CH$_2$F—CF=CH—CH$_2$F, (Z)-CH$_2$F—CH=CH—CHF$_2$, (E)-CH$_2$F—CH=CH—CHF$_2$, (Z)-CH$_3$—CH=CH—CHF$_2$, (E)-CH$_3$—CH=CH—CHF$_2$, (Z)-CH$_3$—CH=CF—CH$_2$F, (E)-CH$_3$—CH=CF—CH$_2$F, (Z)-CH$_3$—CF=CH—CH$_2$F, (E)-CH$_3$—CF=CH—CH$_2$F, (Z)-CH$_3$—CF=CF—CH$_3$, (E)-CH$_3$—CF=CF—CH$_3$, (Z)-CH$_2$F—CH=CH—CH$_2$F, (E)-CH$_2$F—CH=CH—CH$_2$F, (Z)-CH$_3$—CH=CH—CH$_2$F, (E)-CH$_3$—CH=CH—CH$_2$F, (Z)-CH$_3$—CH=CF—CH$_3$, and (E)-CH$_3$—CH=CF—CH$_3$.

These fluoro-2-butenes may be used singly or in combination of two or more of them. The above fluoro-2-butenes include E/Z-geometric isomers as described above, and any fluoro-2-butene in each geometric isomer form can be used in the method for storing a fluoro-2-butene pertaining to the present embodiment.

When a fluoro-2-butene is stored in a container, a gas consisting only of the fluoro-2-butene may be stored in a container, or a mixed gas containing the fluoro-2-butene and a dilution gas may be stored in a container. As the dilution gas, at least one gas selected from nitrogen gas (N2), helium (He), neon (Ne), argon (Ar), krypton (Kr), and xenon (Xe) can be used. The content of the dilution gas is preferably 90% by volume or less and more preferably 50% by volume or less relative to the total volume of the gases stored in a container.

Container

The container in which a fluoro-2-butene is stored may be any container that can store a fluoro-2-butene and be sealed, and the shape, the size, the material, and the like are not specifically limited. The material of the container may be, for example, a metal, ceramics, or a resin.

Examples of the metal include manganese steel, chrome molybdenum steel, stainless steel, Hastelloy (registered trademark), and Inconel (registered trademark).

Impurity

The fluoro-2-butene pertaining to the present embodiment contains or does not contain hydrogen fluoride as an impurity. The fluoro-2-butene is stored in a container in which the concentration of hydrogen fluoride is 100 ppm by volume or less in a gas phase portion when the fluoro-2-butene contains hydrogen fluoride. As described above, this condition suppresses the isomerization reaction of a fluoro-2-butene, and consequently, the fluoro-2-butene is unlikely to be isomerized during storage. When the concentration of hydrogen fluoride in a gas phase portion is not more than the above concentration, the concentration of hydrogen fluoride in a liquid phase portion is also sufficiently low.

Hydrogen fluoride may be generated in a production process of a fluoro-2-butene. The concentration of hydrogen fluoride in a fluoro-2-butene can be determined by using an infrared spectrometer, and the not containing hydrogen fluoride means that hydrogen fluoride cannot be quantified by using an infrared spectrometer.

To suppress isomerization reaction of a fluoro-2-butene during storage, the concentration of hydrogen fluoride in a gas phase portion is required to be 100 ppm by volume or less, but is preferably 50 ppm by volume or less and more preferably 10 ppm by volume or less.

The concentration of hydrogen fluoride in a gas phase portion may be 1 ppm by volume or more.

Method for Producing Fluoro-2-Butene Containing Hydrogen Fluoride at Low Concentration A fluoro-2-butene containing hydrogen fluoride at a low concentration may be produced by any method, and examples of the method include a method of removing hydrogen fluoride from a fluoro-2-butene containing hydrogen fluoride at a high concentration. Hydrogen fluoride may be removed from a fluoro-2-butene by any method, and a known method may be used. Examples of the method include a method of bringing a fluoro-2-butene into contact with an adsorbent and allowing the adsorbent to adsorb hydrogen fluoride, a method of bringing a fluoro-2-butene into contact with a reactant and allowing the reactant to react with hydrogen fluoride, and a separation method by distillation. Specific examples of the adsorbent include molecular sieves and metal fluorides such as sodium fluoride.

Pressure Conditions During Storage

Pressure conditions during storage in the method for storing a fluoro-2-butene pertaining to the present embodiment are not specifically limited as long as a fluoro-2-butene can be sealed and stored in a container, but the pressure is preferably 0.05 MPa or more and 5 MPa or less and more preferably 0.1 MPa or more and 3 MPa or less. When the pressure conditions are within the above range, a fluoro-2-butene can be allowed to pass without warming through a container that is connected to a dry etching system.

Temperature Conditions During Storage

Temperature conditions during storage in the method for storing a fluoro-2-butene pertaining to the present embodiment are not specifically limited, but the temperature is preferably −20° C. or more and 50° C. or less and more preferably 0° C. or more and 40° C. or less. At a temperature of −20° C. or more during storage, a container is unlikely to deform and thus is unlikely to lose the airtightness. This reduces the possibility of oxygen, water, or the like entering the container. If oxygen, water, or the like entered a container, polymerization reaction or decomposition reaction of a fluoro-2-butene could be accelerated. At a temperature of 50° C. or less during storage, polymerization reaction or decomposition reaction of a fluoro-2-butene is suppressed.

Etching

The fluoro-2-butene pertaining to the present embodiment can be used as an etching gas. When an etching gas containing the fluoro-2-butene pertaining to the present embodiment is used in an etching process for producing a semiconductor having a film containing silicon (Si), a protective film is formed on a mask or a side wall, and thus etching selectivity is improved.

An etching gas containing the fluoro-2-butene pertaining to the present embodiment can be used in both plasma etching with plasma and plasmaless etching without plasma.

Examples of the plasma etching include reactive ion etching (RIE), inductively coupled plasma (ICP) etching, capacitively coupled plasma (CCP) etching, electron cyclotron resonance (ECR) plasma etching, and microwave plasma etching.

In plasma etching, plasma may be generated in a chamber in which a member to be etched is placed, or a plasma generation chamber may be installed separately from a chamber in which a member to be etched is placed (i.e., remote plasma may be used).

EXAMPLES

The present invention will next be described more specifically with reference to examples and comparative examples. Fluoro-2-butenes containing hydrogen fluoride at various concentrations were prepared. Fluoro-2-butene preparation examples will be described below.

Preparation Example 1

A manganese steel tank having a volume of 10 L and four manganese steel cylinders each having a volume of 1 L were prepared. These cylinders are called cylinder A, cylinder B, cylinder C, and cylinder D. The tank was filled with 5,000 g of (Z)-1,1,1,4,4,4-hexafluoro-2-butene (boiling point: 33° C.) and was cooled at 0° C. for liquefaction, and a liquid phase portion and a gas phase portion were formed at about 100 kPa. The cylinders A, B, C, and D were depressurized to 1 kPa or less by using a vacuum pump and then were cooled to –78° C.

A SUS tube having a diameter of 1 inch and a length of 30 cm was filled with 100 mL of molecular sieve 5A manufactured by Union Showa. The SUS tube was then connected to the tank.

From the upper outlet where the gas phase portion was present in the tank, 500 g of (Z)-1,1,1,4,4,4-hexafluoro-2-butene gas was extracted and supplied to the SUS tube. The (Z)-1,1,1,4,4,4-hexafluoro-2-butene gas that passed through the SUS tube was collected in the cylinder A at a reduced pressure.

The flow rate of the gas passing through the SUS tube was adjusted to 500 mL/min by using a mass flow controller. The amount of (Z)-1,1,1,4,4,4-hexafluoro-2-butene gas collected in the cylinder A was 491 g.

The (Z)-1,1,1,4,4,4-hexafluoro-2-butene collected in the cylinder A is regarded as sample 1-1. The (Z)-1,1,1,4,4,4-hexafluoro-2-butene gas collected in the cylinder A was extracted from the upper outlet, and the concentration of hydrogen fluoride was determined by using an infrared spectrometer. The result is shown in Table 1. Measurement conditions of the infrared spectrometer were as follows:

Infrared spectrometer: Nicolet iS10 FT-IR spectrometer manufactured by Thermo Fisher Scientific
Cumulative number: 128 times
Mirror speed: 0.6329
Optical path length: 3 m
Gas cell material: SUS316
Gas cell temperature: 100° C.
Measurement wavelength range: 800 to 5,000 cm$^{-1}$
Hydrogen fluoride measurement wavelength: 4,038 cm$^{-1}$

TABLE 1

| | Hydrogen fluoride concentration (ppm by volume) |
| --- | --- |
| Sample 1-1 | 10 or less |
| Sample 1-2 | 34 |

6

TABLE 1-continued

| | Hydrogen fluoride concentration (ppm by volume) |
| --- | --- |
| Sample 1-3 | 89 |
| Sample 1-4 | 155 |

Next, the temperature of the cylinder A was raised to about 0° C., and a liquid phase portion and a gas phase portion were formed. From the upper outlet where the gas phase portion was present in the cylinder A, 100 g of (Z)-1,1,1,4,4,4-hexafluoro-2-butene gas was extracted and transferred to the cylinder B at a reduced pressure. From the tank, 10 g of (Z)-1,1,1,4,4,4-hexafluoro-2-butene gas was extracted and transferred to the cylinder B at a reduced pressure. The temperature of the cylinder B was then raised to room temperature and was allowed to stand for 24 hours. The (Z)-1,1,1,4,4,4-hexafluoro-2-butene after standing is regarded as sample 1-2. From the upper outlet where the gas phase portion was present in the cylinder B after standing, the (Z)-1,1,1,4,4,4-hexafluoro-2-butene gas was extracted, and the concentration of hydrogen fluoride was determined by using an infrared spectrometer. The result is shown in Table 1.

In a similar manner, from the upper outlet where the gas phase portion was present in the cylinder A, 100 g of (Z)-1,1,1,4,4,4-hexafluoro-2-butene gas was extracted and transferred to the cylinder C at a reduced pressure. From the tank, 100 g of (Z)-1,1,1,4,4,4-hexafluoro-2-butene gas was extracted and transferred to the cylinder C at a reduced pressure. The temperature of the cylinder C was then raised to room temperature and was allowed to stand for 24 hours. The (Z)-1,1,1,4,4,4-hexafluoro-2-butene after standing was regarded as sample 1-3. From the upper outlet where the gas phase portion was present in the cylinder C after standing, the (Z)-1,1,1,4,4,4-hexafluoro-2-butene gas was extracted, and the concentration of hydrogen fluoride was determined by using an infrared spectrometer. The result is shown in Table 1.

In a similar manner, from the upper outlet where the gas phase portion was present in the cylinder A, 100 g of (Z)-1,1,1,4,4,4-hexafluoro-2-butene gas was extracted and transferred to the cylinder D at a reduced pressure. From the tank, 200 g of (Z)-1,1,1,4,4,4-hexafluoro-2-butene gas was extracted and transferred to the cylinder D at a reduced pressure. The temperature of the cylinder D was then raised to room temperature and was allowed to stand for 24 hours. The (Z)-1,1,1,4,4,4-hexafluoro-2-butene after standing was regarded as sample 1-4. From the upper outlet where the gas phase portion was present in the cylinder D after standing, the (Z)-1,1,1,4,4,4-hexafluoro-2-butene gas was extracted, and the concentration of hydrogen fluoride was determined by using an infrared spectrometer. The result is shown in Table 1.

Preparation Example 2

The same procedure as in Preparation Example 1 was performed except that (E)-1,1,1,4,4,4-hexafluoro-2-butene (boiling point: 9° C.) was used as a fluoro-2-butene, and samples 2-1 to 2-4 were prepared. The concentration of hydrogen fluoride in each sample was determined by using an infrared spectrometer. The results are shown in Table 2.

TABLE 2

| | Hydrogen fluoride concentration (ppm by volume) |
|---|---|
| Sample 2-1 | 10 or less |
| Sample 2-2 | 21 |
| Sample 2-3 | 76 |
| Sample 2-4 | 123 |

Preparation Example 3

The same procedure as in Preparation Example 1 was performed except that (Z)-1,1,1,2,4,4,4-heptafluoro-2-butene (boiling point: 10° C.) was used as a fluoro-2-butene, and samples 3-1 to 3-4 were prepared. The concentration of hydrogen fluoride in each sample was determined by using an infrared spectrometer. The results are shown in Table 3.

TABLE 3

| | Hydrogen fluoride concentration (ppm by volume) |
|---|---|
| Sample 3-1 | 10 or less |
| Sample 3-2 | 33 |
| Sample 3-3 | 86 |
| Sample 3-4 | 141 |

Preparation Example 4

The same procedure as in Preparation Example 1 was performed except that (E)-1,1,1,2,4,4,4-heptafluoro-2-butene (boiling point: 10° C.) was used as a fluoro-2-butene, and samples 4-1 to 4-4 were prepared. The concentration of hydrogen fluoride in each sample was determined by using an infrared spectrometer. The results are shown in Table 4.

TABLE 4

| | Hydrogen fluoride concentration (ppm by volume) |
|---|---|
| Sample 4-1 | 10 or less |
| Sample 4-2 | 38 |
| Sample 4-3 | 95 |
| Sample 4-4 | 173 |

Preparation Example 5

The same procedure as in Preparation Example 1 was performed except that (Z)-1,1,1,2,3,4,4,4-octafluoro-2-butene (boiling point: 1° C.) was used as a fluoro-2-butene, and samples 5-1 to 5-4 were prepared. The concentration of hydrogen fluoride in each sample was determined by using an infrared spectrometer. The results are shown in Table 5.

TABLE 5

| | Hydrogen fluoride concentration (ppm by volume) |
|---|---|
| Sample 5-1 | 10 or less |
| Sample 5-2 | 28 |

TABLE 5-continued

| | Hydrogen fluoride concentration (ppm by volume) |
|---|---|
| Sample 5-3 | 71 |
| Sample 5-4 | 116 |

Preparation Example 6

The same procedure as in Preparation Example 1 was performed except that (E)-1,1,1,2,3,4,4,4-octafluoro-2-butene (boiling point: 8° C.) was used as a fluoro-2-butene, and samples 6-1 to 6-4 were prepared. The concentration of hydrogen fluoride in each sample was determined by using an infrared spectrometer. The results are shown in Table 6.

TABLE 6

| | Hydrogen fluoride concentration (ppm by volume) |
|---|---|
| Sample 6-1 | 10 or less |
| Sample 6-2 | 31 |
| Sample 6-3 | 82 |
| Sample 6-4 | 151 |

Example 1

The cylinder A was allowed to stand at 20° C. for 30 days, and then from the gas phase portion of the cylinder A, (Z)-1,1,1,4,4,4-hexafluoro-2-butene gas was extracted and analyzed by gas chromatography to quantify the concentration of (E)-1,1,1,4,4,4-hexafluoro-2-butene in sample 1-1. As a result, (E)-1,1,1,4,4,4-hexafluoro-2-butene, which is the isomerization reaction product of (Z)-1,1,1,4,4,4-hexafluoro-2-butene, was not detected.

Measurement conditions of the gas chromatography were as follows:

Gas chromatograph: GC-2014 manufactured by Shimadzu Corporation

Column: CarbopackB phase 1% sp-1000

Injection temperature: 200° C.

Column temperature: 150° C.

Detector: FID

Detector temperature: 200° C.

Carrier gas: helium

Detection limit: 1 ppm by mass

Examples 2 to 18 and Comparative Examples 1 to 6

Analysis objects and analysis results in Examples 2 to 18 and Comparative Examples 1 to 6 are listed in Table 7 in comparison with those in Example 1. In other words, substantially the same analysis as in Example 1 was performed except the items listed in Table 7.

TABLE 7

| | Sample/cylinder | Fluoro-2-butene | Geometric isomer concentration (% by mass) |
|---|---|---|---|
| Ex. 1 | 1-1/A | (Z)-1,1,1,4,4,4-Hexafluoro-2-butene | Not detected |
| Ex. 2 | 1-2/B | " | Not detected |
| Ex. 3 | 1-3/C | " | Not detected |
| Comp. Ex. 1 | 1-4/D | " | 3 |
| Ex. 4 | 2-1/A | (E)-1,1,1,4,4,4-Hexafluoro-2-butene | Not detected |
| Ex. 5 | 2-2/B | " | Not detected |
| Ex. 6 | 2-3/C | " | Not detected |
| Comp. Ex. 2 | 2-4/D | " | 2 |
| Ex. 7 | 3-1/A | (Z)-1,1,1,2,4,4,4-Heptafluoro-2-butene | Not detected |
| Ex. 8 | 3-2/B | " | Not detected |
| Ex. 9 | 3-3/C | " | Not detected |
| Comp. Ex. 3 | 3-4/D | " | 3 |
| Ex. 10 | 4-1/A | (E)-1,1,1,2,4,4,4-Heptafluoro-2-butene | Not detected |
| Ex. 11 | 4-2/B | " | Not detected |
| Ex. 12 | 4-3/C | " | Not detected |
| Comp. Ex. 4 | 4-4/D | " | 4 |
| Ex. 13 | 5-1/A | (Z)-1,1,1,2,3,4,4,4-Octafluoro-2-butene | Not detected |
| Ex. 14 | 5-2/B | " | Not detected |
| Ex. 15 | 5-3/C | " | Not detected |
| Comp. Ex. 5 | 5-4/D | " | 3 |
| Ex. 16 | 6-1/A | (E)-1,1,1,2,3,4,4,4-Octafluoro-2-butene | Not detected |
| Ex. 17 | 6-2/B | " | Not detected |
| Ex. 18 | 6-3/C | " | Not detected |
| Comp. Ex. 6 | 6-4/D | " | 3 |

The invention claimed is:

1. A method for storing a fluoro-2-butene comprising storing the fluoro-2-butene in a container, wherein the fluoro-butene is represented by general formula $C_4H_xF_y$, where x is 0 or more and 7 or less, y is 1 or more and 8 or less, and x+y is 8, wherein the fluoro-2-butene contains or does not contain hydrogen fluoride as an impurity, and a concentration of hydrogen fluoride is 100 ppm by volume or less in a gas phase portion when the fluoro-2-butene contains hydrogen fluoride.

2. The method for storing a fluoro-2-butene according to claim 1, wherein the fluoro-2-butene is at least one selected from (Z)-1,1,1,4,4,4-hexafluoro-2-butene, (E)-1,1,1,4,4,4-hexafluoro-2-butene, (Z)-1,1,1,2,4,4,4-heptafluoro-2-butene, (E)-1,1,1,2,4,4,4-heptafluoro-2-butene, (Z)-1,1,1,2,3,4,4,4-octafluoro-2-butene, and (E)-1,1,1,2,3,4,4,4-octafluoro-2-butene.

3. The method for storing a fluoro-2-butene according to claim 1, wherein the fluoro-2-butene is stored at a temperature of –20° C. or more and 50° C. or less.

4. The method for storing a fluoro-2-butene according to claim 2, wherein the fluoro-2-butene is stored at a temperature of –20° C. or more and 50°° C. or less.

5. The method for storing a fluoro-2-butene according to claim 1, wherein the fluoro-2-butene contains hydrogen fluoride as an impurity, and the fluoro-2-butene is stably stored by suppressing isomerization of the fluoro-2-butene.

* * * * *